US012745768B2

(12) United States Patent
Hansen et al.

(10) Patent No.: US 12,745,768 B2
(45) Date of Patent: Sep. 29, 2026

(54) DEVICES AND METHODS FOR REGULATING TEMPERATURE OF ORGANS DURING OR BEFORE SURGICAL PROCEDURES

(71) Applicant: THE BOARD OF TRUSTEES OF THE LELAND STANFORD JUNIOR UNIVERSITY, Stanford, CA (US)

(72) Inventors: Keith Hansen, San Francisco, CA (US); Victoria Cheng-Tan Wu, San Francisco, CA (US); Nishant Mukesh Doctor, Pflugerville, TX (US); Alexander David Sackeim, San Francisco, CA (US); George Korir, Palo Alto, CA (US)

(73) Assignee: The Board of Trustees of the Leland Standford Junior University, Stanford, CA (US)

( * ) Notice: Subject to any disclaimer, the term of this patent is extended or adjusted under 35 U.S.C. 154(b) by 448 days.

(21) Appl. No.: 18/369,381

(22) Filed: Sep. 18, 2023

(65) Prior Publication Data

US 2024/0000067 A1 Jan. 4, 2024

Related U.S. Application Data

(63) Continuation of application No. PCT/US2022/021020, filed on Mar. 18, 2022.

(Continued)

(51) Int. Cl.
*A01N 1/162* (2025.01)
*A01N 1/122* (2025.01)

(Continued)

(52) U.S. Cl.
CPC ............ *A01N 1/162* (2025.01); *A01N 1/122* (2025.01); *A01N 1/148* (2025.01); *A61F 7/10* (2013.01); *A61F 2007/101* (2013.01)

(58) Field of Classification Search
CPC ........ A01N 1/162; A01N 1/122; A01N 1/148; A01N 1/146; A01N 1/144; A61F 7/10;
(Continued)

(56) References Cited

U.S. PATENT DOCUMENTS 2,954,891 A * 10/1960 Imber ................ B65D 81/3834 220/592.2
3,791,547 A * 2/1974 Branscum ................. F25D 3/08 220/592.2

(Continued)

*Primary Examiner* — Kareen K Thomas
(74) *Attorney, Agent, or Firm* — William A. English; Vista IP Law Group LLP

(57) ABSTRACT

Devices are provided for regulating the temperature of an organ being transplanted that includes a housing including one or more walls surrounding a cavity sized to receive an organ and an opening for accessing the cavity. The walls include an inner layer defining an inner surface for contacting the organ placed in the cavity, an outer layer defining an outer surface of the housing, and a cooling layer between the inner and outer layers, e.g., including a phase-change material configured to absorb thermal energy from the organ within the cavity through the inner layer, e.g., to maintain the organ within a target temperature range before and/or during a transplantation procedure. Optionally, the device may include one or more additional features, e.g., a handle to facilitate manipulation, one or more straps securable across the opening to secure the organ, and/or a temperature sensor to monitor the temperature of the organ.

26 Claims, 11 Drawing Sheets

Related U.S. Application Data

(60) Provisional application No. 63/265,834, filed on Dec. 21, 2021, provisional application No. 63/200,657, filed on Mar. 19, 2021.

(51) Int. Cl.
*A01N 1/148* (2025.01)
*A61F 7/10* (2006.01)

(58) Field of Classification Search
CPC ................ A61F 2007/101; A61F 7/106; A61F 2007/0056; A61F 2007/0075; A61F 2007/0086; A61F 2007/0093; A61F 2007/0095; A61B 2017/00969
See application file for complete search history.

(56) References Cited

U.S. PATENT DOCUMENTS 5,403,095 A * 4/1995 Melk ...................... A45C 11/20 383/110
5,906,290 A * 5/1999 Haberkorn ......... B65D 81/3886 190/110
6,105,844 A * 8/2000 Walters .................. A45C 11/20 206/547
6,391,262 B1 * 5/2002 Brinton .................. G01N 33/84 422/402
7,162,890 B2 * 1/2007 Mogil ................ B65D 81/3858 62/530
8,043,004 B2 * 10/2011 Mogil ...................... A45C 5/02 220/592.2
8,317,047 B2 * 11/2012 Vanderberg ............... F25D 3/06 220/666
8,550,288 B2 * 10/2013 Briar ...................... B65D 25/02 220/62.12
9,567,150 B2 * 2/2017 Lachance ............... B65D 81/38
10,551,110 B2 * 2/2020 Waltermire ........ B65D 81/3888
10,583,978 B2 * 3/2020 Longley ............. B65D 81/3897
10,852,047 B2 * 12/2020 Alexander .............. F25B 21/02
11,160,569 B2 * 11/2021 Razavi ................... A61B 17/24
2006/0182160 A1 * 8/2006 Watts ........................ G02F 1/15 372/43.01
2008/0008987 A1 * 1/2008 Bianco ................... A01N 1/144 604/113
2008/0164265 A1 * 7/2008 Conforti ............ B65D 81/3823 220/592.2
2018/0328644 A1 * 11/2018 Rizzo .................... F25D 11/003
2021/0190742 A1 * 6/2021 Sanson .................. G01N 31/22
2022/0211219 A1 * 7/2022 Owens .................. A47J 47/145

* cited by examiner

DEVICES AND METHODS FOR REGULATING TEMPERATURE OF ORGANS DURING OR BEFORE SURGICAL PROCEDURES

RELATED APPLICATION DATA

The present application is a continuation of co-pending International Application No. PCT/US2022/021020, filed Mar. 18, 2022, which claims benefit of U.S. provisional application Ser. No. 63/200,657, filed Mar. 19, 2021, and 63/265,834, filed Dec. 21, 2021, the entire disclosures of which are expressly incorporated by reference.

STATEMENT REGARDING FEDERALLY SPONSORED RESEARCH AND DEVELOPMENT

None.

TECHNICAL FIELD

The present application relates generally to devices for use during surgical procedures, e.g., organ transplant procedures, and, more particularly, to temperature regulating devices to maintain desired preoperative and/or intraoperative temperatures to transplanted organs, such as kidneys, and to methods for using such devices.

BACKGROUND

Kidney transplantation is the best current treatment for kidney failure. However, one out of three (33%) of kidney transplant patients experience delayed graft function ("DGF"), which is defined as a transplant recipient requiring dialysis within seven days of transplantation surgery. Patients that develop DGF have longer hospitalizations, increased rates of rejection, and shorter graft survival by an estimated three to five (3-5) years. Premature graft failure in these patients means a return to long-term dialysis and increased morbidity, from continued immunosuppression therapy or transplantectomy, without the benefits of transplantation.

The mechanism underlying DGF is thought to be related to ischemic damage sustained in the time period between organ procurement and transplantation. Renal metabolism is predominantly aerobic which makes it especially susceptible to anoxic damage and ischemia. Hypothermia protects against anoxia by significantly reducing the energy dependent metabolic activities of the kidney. Optimal renal hypothermia for transplantation is achieved at about one to two degrees Celsius (1-2° C.), and about four to eight degrees Celsius (4-8° C.) for machine based cold-perfusion. Transplant teams use this preservative effect as soon as an organ is removed from a donor and during transport. Cadaver kidneys are routinely packaged and maintained at less than four degrees Celsius (4° C.). However, during the recipient transplantation surgery, there are no effective methods to prevent re-warming and the anoxic damage that subsequently occurs. Kidney warming above the threshold of necrosis begins as early as ten minutes into a surgical anastomosis procedure. Warming of a donor kidney during the sew-in period of a transplant, i.e., second warm ischemia time ("SWIT"), is independently associated with higher rates of delayed graft function, premature graft failure, and a lower acceptance rate of higher-risk kidneys by surgeons.

SWIT is protracted in patients and kidneys with complex anatomy, pediatric patients, in minimally invasive surgery, and in patients with obesity.

Reducing SWIT to less than thirty minutes (30 min) reduces the risk of DGF by 3.5-fold. Furthermore, elimination of warm ischemia by graft cooling during implantation to a target temperature of about four degrees Celsius (4° C.) reduces metabolism in the majority of cells to about five to eight percent (5-8%) of normal levels and diminishes enzyme activity, thereby minimizing ischemic injury. This significantly reduces the of DGF and improves organ function.

There remains a need for a reliable approach to control the temperature of organs during transplantation surgery. Devices or methods capable of regulating the temperature of kidneys or other organs, e.g., before and/or during transplantation procedures, would be useful.

SUMMARY

The present application is directed to medical devices related to organ transplant procedures, and, more particularly, to devices for facilitating surgery involving transplanted organs and/or for hypothermic treatment of organs, e.g., to maintain desired preoperative and/or intraoperative temperatures to transplanted organs, such as kidneys, and to methods for using such devices, e.g., to improve workflow during surgical procedures.

The devices and methods herein may facilitate intraoperative handling of a kidney or other organ during surgery. Inadvertent slippage of the organ may be reduced and the devices may be attached to retractors (e.g., Bookwalter or Thompson retractors) and/or attached or clamped to the surgical drapes, which may free both hands of an assistant to more effectively assist a surgeon during vascular anastomosis. Additional device attributes, such as a retraction handle, temperature sensor, and an orientation indicator, may provide visual and tactile support to the surgeon during the anastomosis. In some examples, the devices have no tubing or attachments that could impede a transplantation surgeon as they work. The devices may be less bulky than conventional devices, particularly those that have external tubing that may get in the way, e.g., of the fine sutures that are used during anastomosis. Conventional devices may not cool the organ for long enough and/or consistently, may change the workflow of the procedure, and may not be used easily in obese patients or patients with difficult anatomy.

In accordance with one example, a device is provided for regulating the temperature of an organ being transplanted from a donor to a recipient, e.g., preoperatively or intraoperatively, that includes a housing including one or more walls surrounding an interior cavity sized to receive an organ and an opening for accessing the cavity, wherein one or more of the walls includes an inner layer defining an inner surface for contacting the organ placed in the cavity, an outer, e.g., insulation, layer defining an outer surface of the housing, and a cooling layer between the inner and outer layers configured to absorb thermal energy from the organ within the cavity through the inner layer.

In accordance with another example, a device is provided for regulating temperature of an organ that includes a housing including one or more walls surrounding an interior cavity sized to receive an organ and an opening for accessing the cavity, one or more of the walls including a cooling layer comprising a phase-change material configured to absorb thermal energy from the organ within the cavity through the inner layer.

Optionally, in any of the devices herein, the outer wall may include material having a low thermal conductivity to minimize exposure of the cooling layer to exterior temperatures.

Optionally, in any of the devices herein, the inner wall may include material having a high thermal conductivity to maximize exposure of the organ to the cooling layer.

Optionally, the devices may include one or more fasteners for at least partially closing the opening to secure the organ received within the cavity, e.g., a pair of straps extending from one edge of the opening adjacent one another that may be secured to the housing across the opening.

Optionally, the devices may include a handle extending from the housing to facilitate manipulation of the housing, e.g., that extends from a back wall of the housing generally opposite the opening.

Optionally, the devices may include an indicator on the housing configured to provide a visual indication of an anatomical orientation of the organ received within the cavity.

Optionally, the devices may include a temperature sensor adjacent to the inner surface for measuring temperature of the organ received in the cavity, and an output device to provide an output of the measured temperature.

Optionally, the devices may include a timer configured to be activated during a surgical procedure to provide an indication of elapsed time during the procedure.

Optionally, the devices may include one or more sensors adjacent the inner surface for measuring one or more characteristics of the organ received in the cavity, such as an ultrasound or doppler sensor, a sensor configured to assess one or more of assess vascular flow metrics, resistive indices, kidney appearance, or to acquire sub-capsular images, and/or a temperature sensor for measuring temperature of the organ received in the cavity. Optionally, the device may include a wireless transmitter for transmitting data acquired by the sensor(s) to a remote device.

Optionally, the devices may include a GPS tracking device mounted on the housing to allow the location of the device to be monitored.

Optionally, the devices may include one or more lights adjacent to the opening, e.g., to illuminate a surgical field adjacent the opening.

In accordance with another example, a method is provided for cooling an organ, providing a housing comprising one or more walls surrounding an interior cavity, wherein one or more of the walls comprises an outer insulative layer and a cooling layer adjacent to an inner surface of the cavity; and placing an organ within the cavity.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

DETAILED DESCRIPTION

Figure 1A:
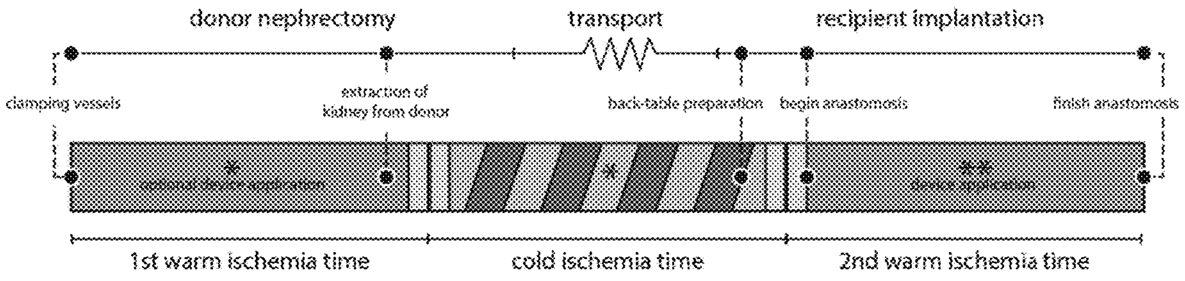
FIGS. 1A and 1B are overview schematics showing the temperature periods involved in current kidney transplant procedures, from clamping the aorta and extraction of the donor kidney to implantation into the recipient, illustrating the periods of first warm ischemia, cold ischemia and second warm ischemia.

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

The kidneys of patients with End-Stage Renal Disease ("ESRD") are not working well enough to sustain life. The current treatment for the patient's life-threatening condition is long-term dialysis or a kidney transplant. A kidney transplant is the optimum treatment for these patients because life expectancy increases significantly for those who receive a transplant when compared to those receiving long-term dialysis.

Figure 1B:
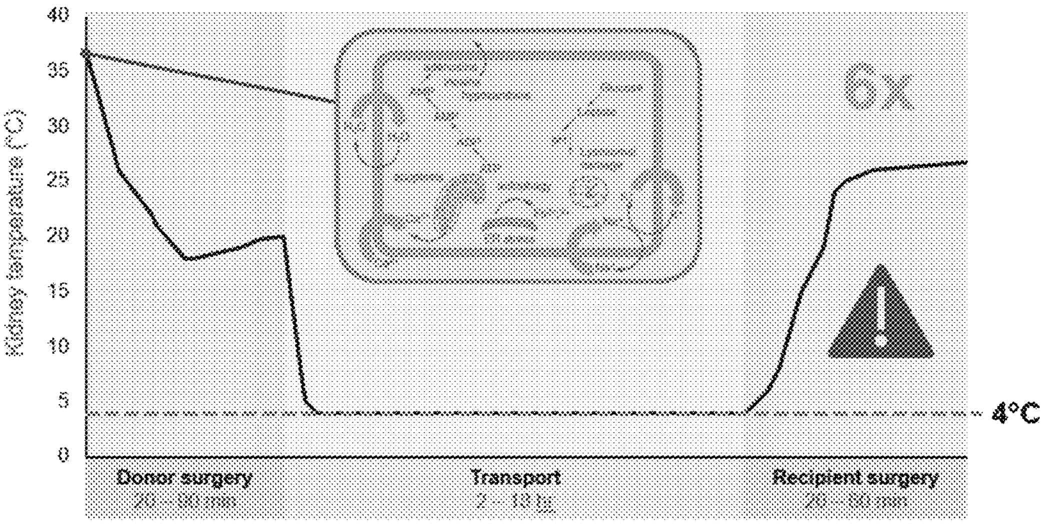

The current standard of care ("SOC") for kidney transplantation begins when a surgeon removes a kidney from a donor. When the kidney stops receiving oxygenated blood, the cells initiate anaerobic metabolism leading to the depletion of ATP stores and release of damaging byproducts. These events cause cell death and organ dysfunction and need to be mitigated for many hours to preserve the viability of the donor kidney for the recipient. Cooling is a well-understood method to mitigate ischemic injury and preserve the viability of a donor kidney. Lowering the temperature of the donor kidney to between about two and six degrees Celsius (2-6° C.) as quickly as possible, without causing the cells to freeze and rupture, slows down anaerobic metabolism, which in turn slows down progression to cell death. For the purpose of discussing current SOC for hypothermic treatment of the recipient's kidney after it has been removed from the donor, FIGS. 1A and 1B show (hypothetical) temperatures of a kidney during three stages of the transplant process: Stage 1—Donor Surgery; Stage 2—Transport; Stage 3—Recipient (i.e., Transplantee) Surgery.

One goal of the clinical teams involved in each stage of the transplantation process is to reduce warm ischemic injury, i.e., the time the kidney spends at elevated temperatures without being perfused with blood and oxygen. In Stage 1, transplant teams attempt to slow down ischemic injury by extracting the kidney from the donor and cooling the organ by putting it on ice immediately or via other methods of cooling. The goal is to reduce the temperature of the kidney from body temperature (displayed as thirty-seven degrees Celsius (37° C.) in FIG. 1B) to the target temperature (e.g., about one to seven degrees Celsius (1-7° C.)) as quickly as possible and reduce the first warm ischemic injury to the organ ("FWII").

In Stage 2, the kidney is transported from the donor to the intended recipient with ESRD. The recipient may be located in the same hospital as the donor or across the country; therefore, the duration of Stage 2 varies typically between about two and eighteen (2-18) hours (or longer). Fortunately, multiple FDA-cleared devices are indicated for safe and effective hypothermic treatment of the kidney during Stage 2. These devices are capable of maintaining the organ at the target temperature during transportation.

Devices are needed for the hypothermic treatment of a donor kidney during Stage 3—Transplantee Surgery. The second warm ischemic injury ("SWII") that occurs during Stage 3 has been linked to poor short- and long-term outcomes for the recipient and premature failure of the transplanted kidney. The SWII also contributes to the reduction in the available pool of donor kidneys since ischemic injury is cumulative, that is, the SWII adds to the FWII. Transplant surgeons are aware of this fact, thus increasing the number of donor kidneys they reject for their patients (e.g., those obtained from donors who die after cardiac events). In addition to the direct injury to the recipient's kidney caused by the SWII, an indirect injury to the recipient may result from the time-sensitive nature of the transplantation procedure. Surgeons are aware of the SWII and thus work to complete anastomosis as quickly as possible, which in turn can lead to mistakes and surgical complications.

Figure 2:
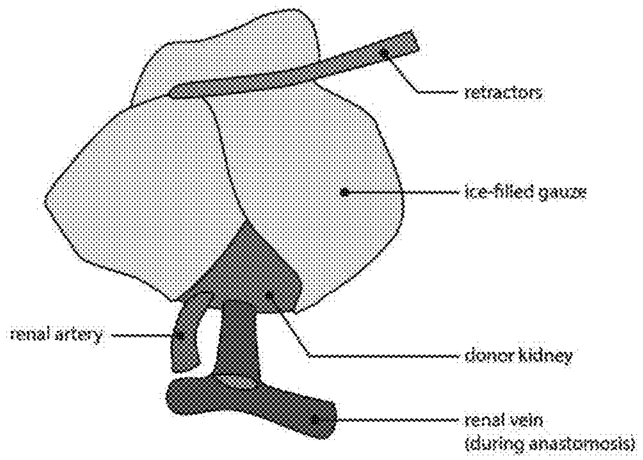
FIG. 2 shows a commonly used technique to cool and provide a gripping surface on a donor kidney using gauze, crushed ice, and surgical clamps and/or retractors.

SOC for mitigating the effects of the SWII during Stage 3 is to wrap the kidney in gauze and ice as the recipient is prepared for surgery, e.g., as shown in FIG. 2. However, this is not uniformly adopted for the anastomosis portion of the surgery due to the technical challenges of completing the step with these ad-hoc cooling methods. When the kidney is no longer surrounded with the gauze and ice, the organ quickly warms and may reach fifteen degrees (15° C.) within ten minutes. As the recipient's kidney warms, it undergoes ischemic injury at a rate six times faster than when it was kept cold. Surgeons may not realize how quickly temperature increases and its impact on the kidney because intraoperative temperature of the organ is not measured during Stage 3 and, thus, they stay focused on completing anastomosis as quickly as possible.

Figure 3:
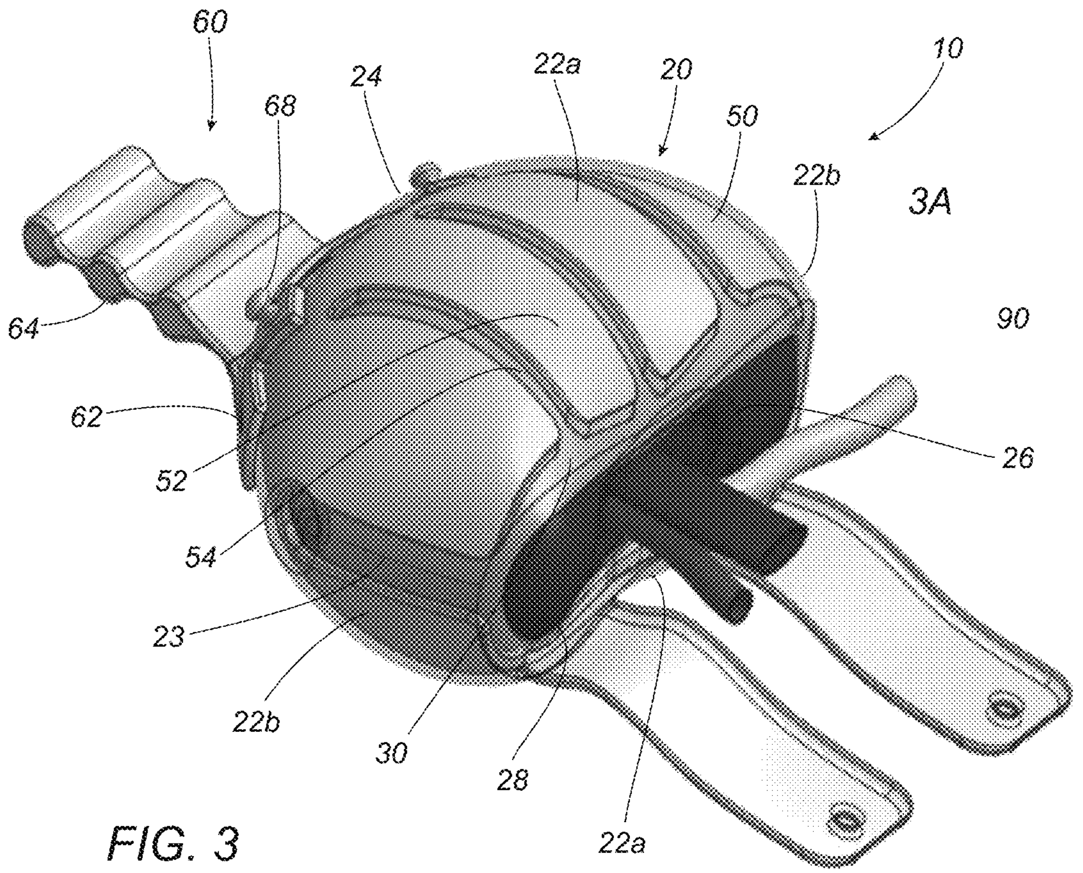
FIG. 3 shows an example of a device for regulating temperature of an organ before and/or during a transplantation procedure.

Turning to FIG. 3, an example of a device 10 is shown for hypothermic treatment of an organ 90, such as a kidney, e.g., for regulating the temperature of an organ 90 being transplanted from a donor to a recipient, particularly preoperatively in Stage 3 and/or intraoperatively during an anastomosis procedure. It will be appreciated that the device 10 may be used during other periods, e.g., to store the organ immediately after removal from the donor (Stage 1), during transportation (Stage 2), and/or preoperatively, e.g., during back-table preparation. In addition, the devices and methods herein may facilitate surgical implantation procedures, e.g., enhancing surgical workflow such as during an anastomosis procedure where vessels of the organ are connected to the recipient's vessels. In addition, the devices and methods herein may facilitate minimally invasive and/or robotic procedures, e.g., to facilitate cooling, positioning, and/or manipulation of an organ during an implantation procedure.

Although the devices and methods herein are generally described with particular reference to kidney transplantation, it will be appreciated that the devices and methods may be used for transplantation of other organs, e.g., hearts, lungs, or livers, or grafts and/or other structures, such as heart valves, vascular grafts, extremities, or other body parts, and the like. Additionally, the devices herein may be used to surround or store bags or other containers of fluid solution, preservation solutions, blood, plasma, medications, and/or other temperature-sensitive materials that are used in transplant or other surgeries (e.g., during procurement, transport, and/or recipient surgery), or in other fields of patient care in order to maintain the material at a desired temperature for a desired duration. For example, the devices may be used to cover or contain preservation solutions to cool them during a procurement period and/or when flushing a donor organ during back-table preparation.

Generally, as shown in FIG. 3, the device 10 includes a housing 20 including one or more walls 22, 24 surrounding an interior cavity or compartment 26 sized to receive the organ 90 and an opening 28 for accessing the cavity 26. For example, the housing 20 may include upper and lower sidewalls 22*a* and end walls 22*b* opposite one another, thereby surrounding the cavity 26, and a back wall 24 opposite the opening 28 to further enclose the cavity 26. In the example shown, the upper and lower walls 22*a* may be longer than the end walls 22*b*, e.g., such that the housing 20 defines an oblong or other elongated shape, e.g., corresponding to the shape of a kidney.

In addition or alternatively, the walls 22, 24 may be rounded and/or otherwise shaped to receive the kidney with minimal airspace within the cavity 26. For example, FIGS. 5A-5D show an alternative device 10' generally similar to device 10, except that the housing 20' has a generally kidney-shaped cross-section, e.g., as best seen in FIG. 5B. As shown, the housing 20' includes a convex or otherwise rounded upper wall 22*a'*, opposite side walls 22*b'*, first and second end walls 22*c'* 22*d'*, and a lower wall 22*e'* including opening 28,' which may be integrally formed together. The side walls 22*b'* may be longer than the end walls 22*c'*, 22*d'*, and the lower wall 22*e'* may have a partially concave or flat shape, thereby defining the kidney-shaped cross-section.

Returning to FIG. 3, the walls 22, 24 of the housing 20 may be integrally formed together, e.g., from flexible material, to provide a jacket or sleeve having a generally fixed size opening 28 through which the organ 90 may be inserted into the cavity 26. Alternatively, one or more gaps, slots, hinges, or other features (not shown) may be provided, e.g., slots 23 along the end walls 24, to allow the housing 20 to be opened to facilitate placement of the organ 90 and then closed around the organ 90, e.g., folded or otherwise wrapped around the organ to minimize space around the organ 90 within the cavity 26. In another alternative, a plurality of devices may be provided, e.g., having different sizes and/or shapes to accommodate different sized organs such that an appropriate device may be selected for a particular organ being transplanted, e.g., to minimize airspace within the cavity 26 around the organ 90.

Figure 3A:
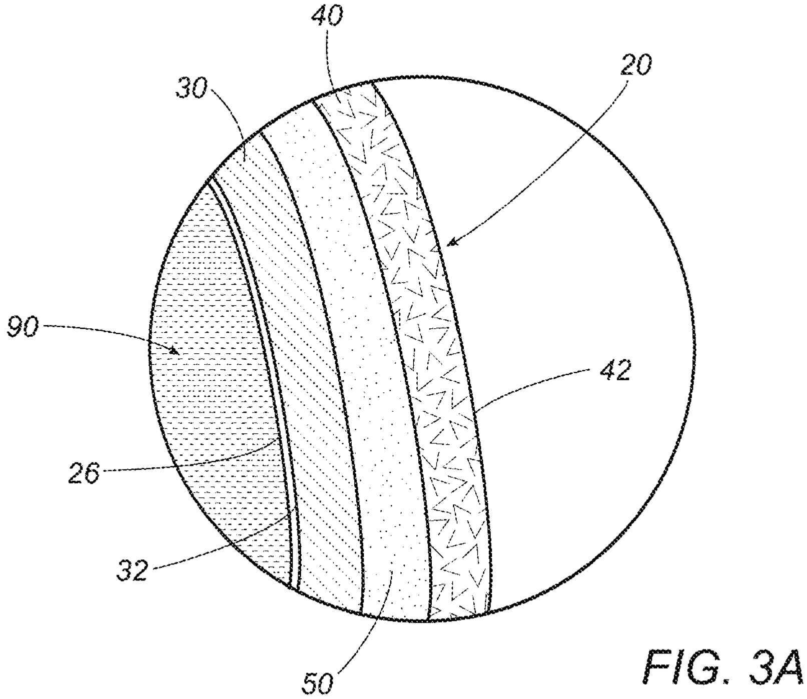
FIG. 3A is a cross-sectional detail showing the construction of the wall of the device of FIG. 3.

With additional reference to FIG. 3A, one or more walls 22 of the housing 20 may be constructed in a multiple layer construction, e.g., encapsulating cooling material, such as a phase-change gel or other coolant within wall(s) of the housing 20. For example, as shown, one or more walls 22 of the housing 20 may include an inner layer 30 defining an inner surface 32 for contacting the organ 90 placed in the cavity 26, an outer layer 40 defining an outer surface 42 of the housing 20, and a cooling layer 50 between the inner and outer layers 30, 40.

In one example, the inner layer 30 and outer layer 40 may be formed from flexible material, e.g., polymer material such as hydrogel, elastomeric material such as silicone, and the like. The material may be elastic and/or otherwise stretchable or may be inelastic, e.g., having a defined size and shape. The inner layer 30 may have a thickness and/or relatively high thermal conductivity to readily transfer thermal energy from the organ 90 received in the cavity 20 to the cooling layer 50. Conversely, the outer layer 40 may have a thickness and/or relatively low thermal conductivity to minimize exposure of the cooling layer 50 to exterior temperatures. The inner and outer layers 30, 40 may be formed separately and then permanently attached together, e.g., by one or more bonding with adhesive, fusing, sonic welding, and the like, or may be integrally formed together, e.g., by molding, casting, 3D printing, and the like.

In addition or alternatively, other materials may be included in the housing 20, e.g., woven textiles, ceramic fibers, and the like, e.g., to provide desired thermal characteristics and/or to provide desired finishes for the inner and/or outer surfaces 32, 42 of the housing 20. Optionally, the outer layer 40 may include one or more additional insulating features, e.g., air pockets, foam fillers, and the like (not shown) to reduce the thermal conductivity of the outer layer 40. In addition or alternatively, one or more walls may include biasing mechanisms, e.g., one or more band springs or other structures (not shown) embedded within or otherwise attached to the wall(s) to provide a desired shape and/or structural integrity to the housing 20, e.g., if the wall(s) are formed from elastic or stretchable material. Optionally, such biasing mechanisms may be expandable, e.g., such that the housing 20 may be stretched or otherwise expanded to accommodate receiving an organ within the cavity 26. Upon release, the biasing mechanism may compress the housing 20, e.g., to minimize airspace around the organ 90 and/or otherwise enhance securing the organ 90 within the housing 20.

The cooling layer 50 may include phase-change material composed to maintain the cavity 26 and the organ 90 therein within a desired temperature range, e.g., between about one and seven degrees Celsius (1-7° C.), between about two and six degrees Celsius (2-6° C.), or about four degrees Celsius (4° C.). The phase-change material may include a phase-change gel, i.e., that absorbs thermal energy by changing from a solid phase to a liquid phase. During this phase change, the phase-change gel maintains a substantially constant temperature, thereby absorbing thermal energy from the organ 90 through the inner layer 30 to maintain the organ 90 within the desired temperature range. Exemplary materials for the phase-change gel may include known biocompatible phase-change gels, such as 1-Decanol (Decyl alcohol), n-tetradecane (n-TD), and the like.

In the example shown in FIG. 3, the phase-change material is sealed within a plurality of cells or regions 52 between the inner layer 30 and outer layer 40 (shown in phantom to illustrate the cooling layer 50), e.g., such that the phase-change material is isolated from the interior cavity 26. As shown in FIG. 3, cells 52 of the cooling layer 50 may be at least partially isolated from one another, e.g., by gaps 54. Such gaps may enhance connection between the inner and outer layers 30, 40 and/or enhance the overall structural integrity of the housing 20. Alternatively, the phase-change material may be provided continuously between the inner and outer layers 30, 40, e.g., sealed therebetween to prevent the phase-change material from escaping during use, e.g., with the inner and outer layers 30, 40 connected together at one or more seams or other connection points (not shown). In another alternative, the cooling layer may be included in only some of the walls of the device. For example, the device 10' shown in FIGS. 5A-5D may include a cooling layer primarily within top wall 22*a*', and end wall 22*c*,' which may sufficiently surround the interior cavity 26' of the housing 20' to sufficiently cool the organ 90 received therein.

In a further alternative, the phase-change material may be received in separate pockets or chambers within the walls of the housing 20, e.g., in sealed packets that may be removable or permanently secured within the housing 20 (not shown). For example, if the device 10 is reusable, the phase-change material from a previous procedure may be removed and replaced with fresh phase-change material, e.g., after cleaning and sterilizing the housing 20. Otherwise, if the device 10 is single-use, the phase-change material may be permanently sealed within the walls of the housing 20 such that the entire device 10 is discarded after a procedure.

The thickness of the cooling layer 50 and location of the phase-change material may be selected to provide a desired volume of phase-change material around the cavity 26 to maintain the desired temperature of the organ 90 for a desired length of time, e.g., between about forty-five and seventy minutes (45-70 min), between about twenty and sixty minutes (20-60 min), between about thirty and sixty minutes (30-60 min), or longer if desired, e.g., for extended transportation time periods. In one example, the cooling layer 50 may have a thickness between about one tenth and three centimeters (0.1-3.0 cm) or between about one and three centimeters (1.0-3.0 cm).

Optionally, the device 10 may include one or more features to facilitate manipulation of the device 10. For example, as shown, a handle 60 may be provided on the housing 20, e.g., removably mounted to the back wall 24, e.g., as best seen in FIGS. 4A-4D. In the example shown, the handle 60 includes a base plate 62 sized and/or shaped to conform to the back wall 24 and a rigid retractor handle 64 extending from the base plate 62, e.g., substantially perpendicular to the base plate 62. As shown the retractor handle 64 may have a blade shape including a plurality of grip features, which may facilitate manipulating the device 10, e.g., during transport and/or during an anastomosis procedure. The retractor handle 64 may also include one or more connectors or other features (not shown), which may facilitate connecting the device to retractors and/or other surgical devices, e.g., to stabilize the device 10 within a surgical field.

The base plate 62 and back wall 24 may include one or more cooperating connectors, e.g., detents, clasps, and the like (not shown), to mechanically secure the handle 60 to the housing 20, while allowing the handle 60 to be removed if desired. In addition, if the housing 20 includes one or more sensors or other electrical components (e.g., as described elsewhere herein), the base plate 62 and back wall 24 may include one or more electrical connectors that are coupled together when the handle 60 is attached to the housing 20. Such a removable handle 60 may facilitate manipulation while being removable when not needed, e.g., to facilitate storage and/minimize the profile of the device 10. Alternatively, the handle 60 may be permanently attached to the housing 20, e.g., to the back wall 24 by one or more of bonding with adhesives, fusing, welding, mechanical connectors, and the like (not shown).

Figure 4A:
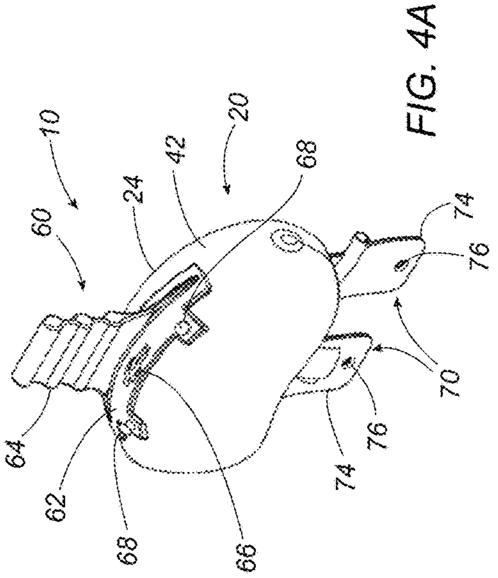
FIGS. 4A-4D are various views of the device of FIG. 3 after receiving an organ and before closing straps to secure the organ therein.

Optionally, as best seen in FIG. 4A, an indicator 66 may be provided on the base plate 62, e.g., to provide a visual indication of an anatomical orientation of the organ 90 received within the cavity 26. For example, as shown, the indicator 66 may be provided on the base plate 62 of the handle 60, which includes a representation of a human body aligned along the length of the housing 20, e.g., parallel to the sidewalls 22*a*. The indicator 66 may facilitate a physician or other user inserting the organ 90 initially into the cavity 26 in an orientation corresponding to the correct anatomical orientation, e.g., with the top of the organ oriented towards the head of the indicator 66. In addition, during an implantation procedure, the surgeon and/or other user may position the device 10 against the recipient with the indicator 66 in the proper orientation relative to the recipient's body before beginning the anastomosis, e.g., as described elsewhere herein. In addition or alternatively, one or more other visual indicators may be provided on other locations on the outer surface 42 of the housing 20, if desired, to further aid in placing the organ 90 into the device 10 and/or during the implantation procedure.

Optionally, the device 10 may include one or more fasteners or other features for at least partially closing the opening 28 and/or otherwise securing an organ 90 received within the cavity 26. For example, as shown in FIG. 3, a pair of straps 70 may be provided adjacent the opening 28 that may be secured across the opening 28. As shown, each strap 70 includes a first end 72 attached to one edge of the opening 29, e.g., permanently attached by one or more of bonding with adhesive, fusing, welding, stitching, and the like, and a second free end 74. The straps 70 may be formed from similar materials to the housing 20, e.g., with or without a cooling layer, as desired.

Figure 4B:
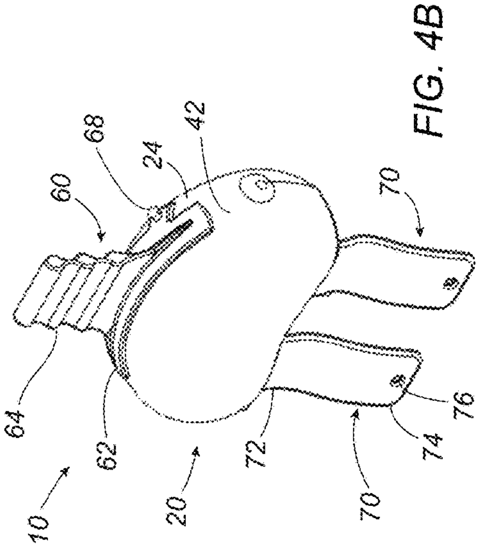
Figure 4C:
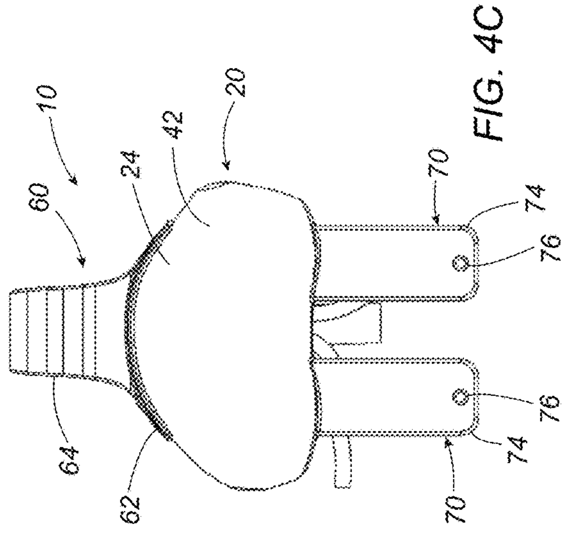
Figure 4D:
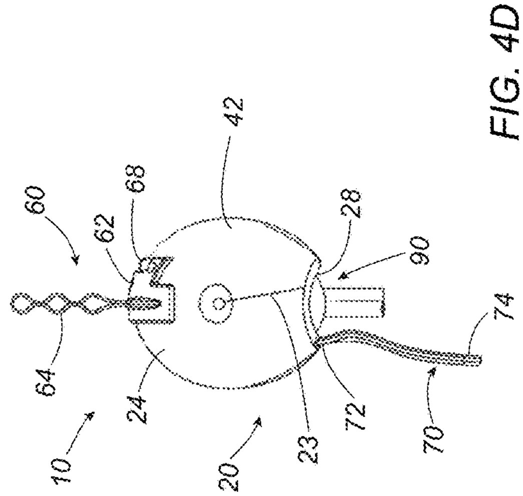
Figure 4F:
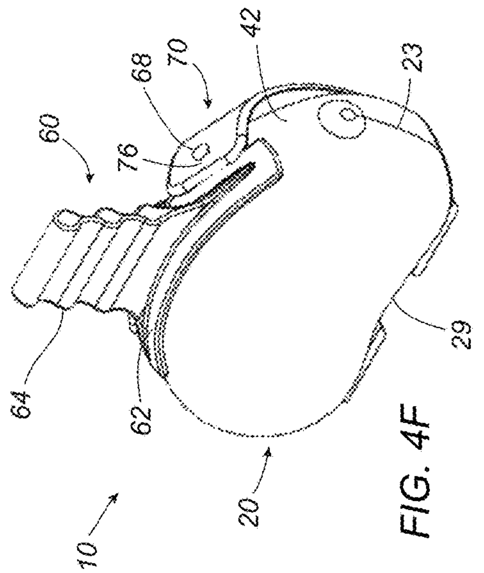
FIGS. 4E-4H are various views of the device of FIG. 3 after securing the straps to secure the organ therein.
Figure 4H:
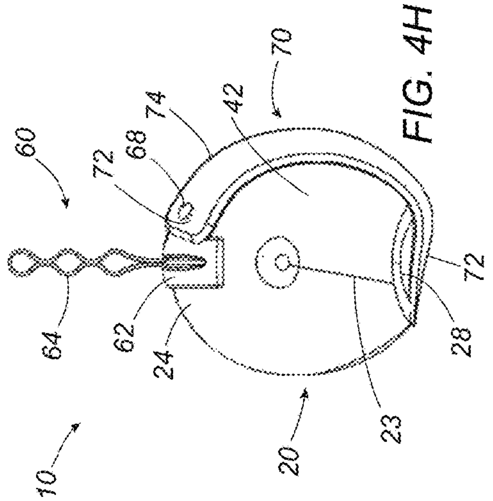
Figure 4E:
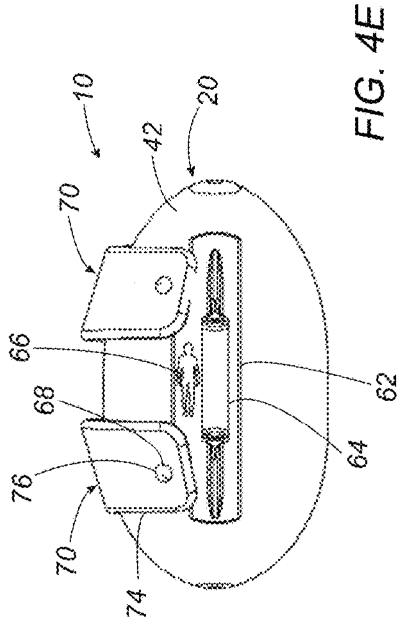
Figure 4G:
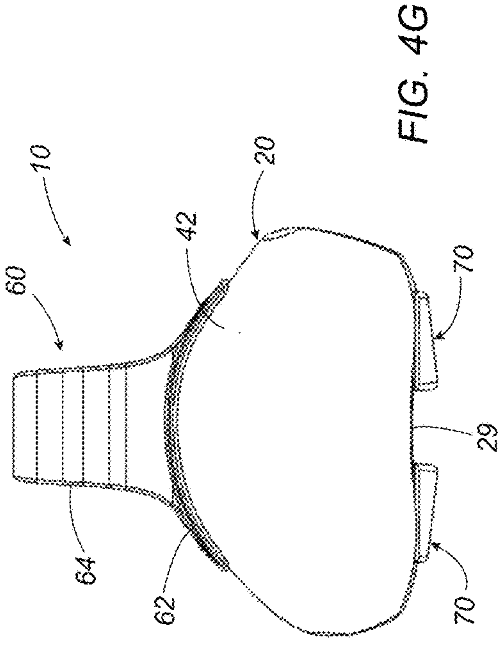

The free ends 74 of the straps 70 and the housing 20 may include cooperating connectors for securing the straps 70 to the housing 20 such that the straps 70 may be extended across the opening 28 and secured, thereby preventing the organ 90 from falling out or being removed from the cavity 26. For example, as best seen in FIGS. 4A-4B, each free end 74 may include an eyelet or other opening 76 and a corresponding post or button 68 may be provided on the base plate 62 of the handle 60 such that the free end 74 may be wrapped around the outer surface 42 of the housing 20 and the post 68 received in the eyelet 76, e.g., as shown in FIGS. 4E-4H. Optionally, if the housing 20 is formed from flexible material, wrapping the straps 70 over the opening 28 and around the outer surface 42 may draw the opposite edges closer together, e.g., to minimize exposure of the organ 90 and/or further secure the organ 90 within the cavity 26.

As shown, the straps 70 are attached along the same edge of the opening 28 and are spaced apart from one another such that a portion 29 of the opening 28 remains open between the straps to allow vessels or other structures 92 from the organ 90 received within the cavity to extend from the housing 20. For example, if the organ 90 is a kidney, the iliac vessels 92 may extend from the central portion 29 of the opening 28, which may facilitate completing an anastomosis procedure without having to remove the kidney 90, as described further elsewhere herein.

Although the eyelets 76 and posts 68 are shown, it will be appreciated that the connectors may be reversed or other connectors may be provided on the free ends 74 of the straps 70 and the housing 20, such as clips, snaps, magnets, and the like (not shown). In addition, the connectors on the housing 20 may be provided at other locations on the outer surface 32, rather than on the base plate 62 of the handle 60, and the lengths of the straps 70 may be modified to accommodate other locations. In addition or alternatively, a plurality of connectors, e.g., a row of posts or eyelets (not shown), may be provided on the housing 20 and/or on the straps 70 that allow the straps 70 to be secured to the housing 20 at one or more locations, e.g., to allow the straps 70 to be tighter and/or further close the opening 28 before securing the connectors.

Figure 5A:
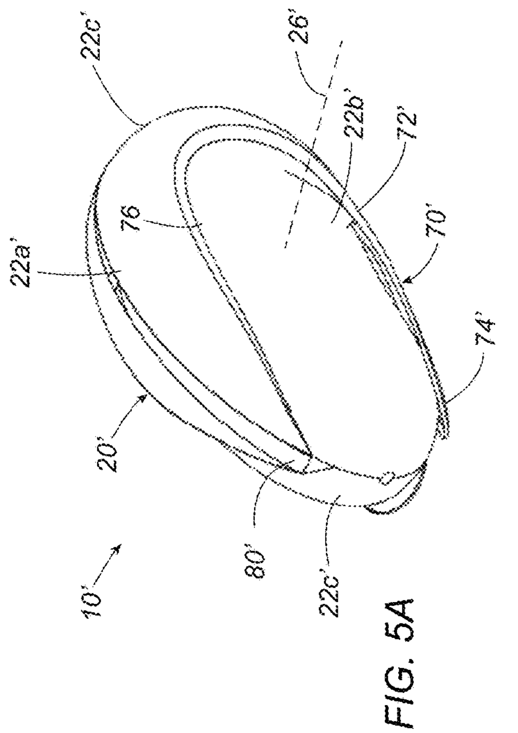
FIGS. 5A-5D show an alternative example of a hypothermic device including an opening in a lower wall of the device housing and straps extending across the lower wall to secure an organ within the device.
Figure 5B:
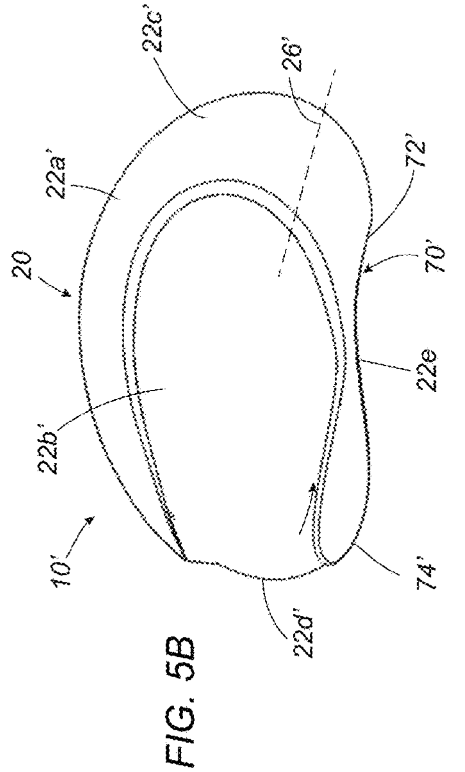
Figure 5C:
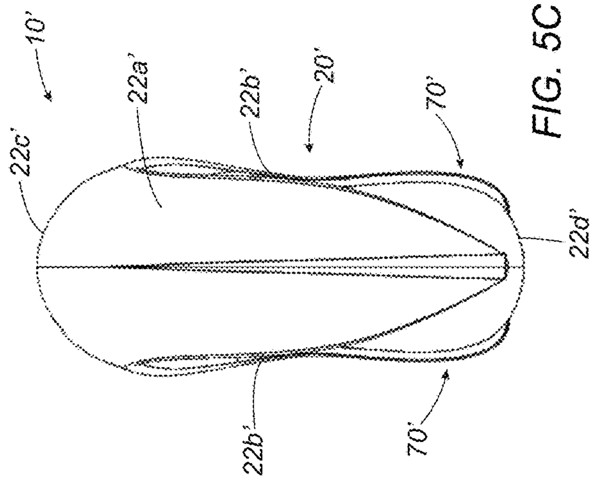
Figure 5D:
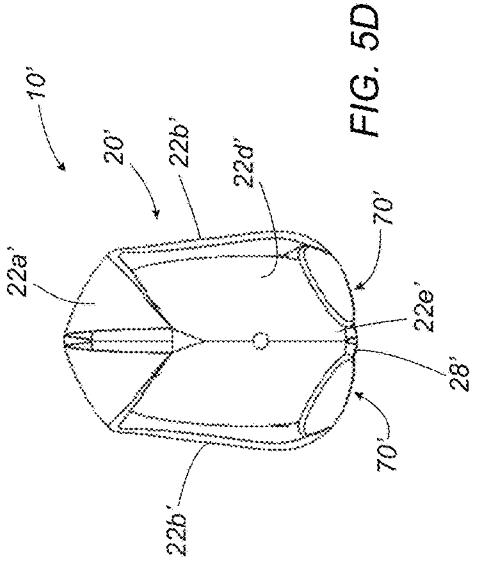
Figure 5E:
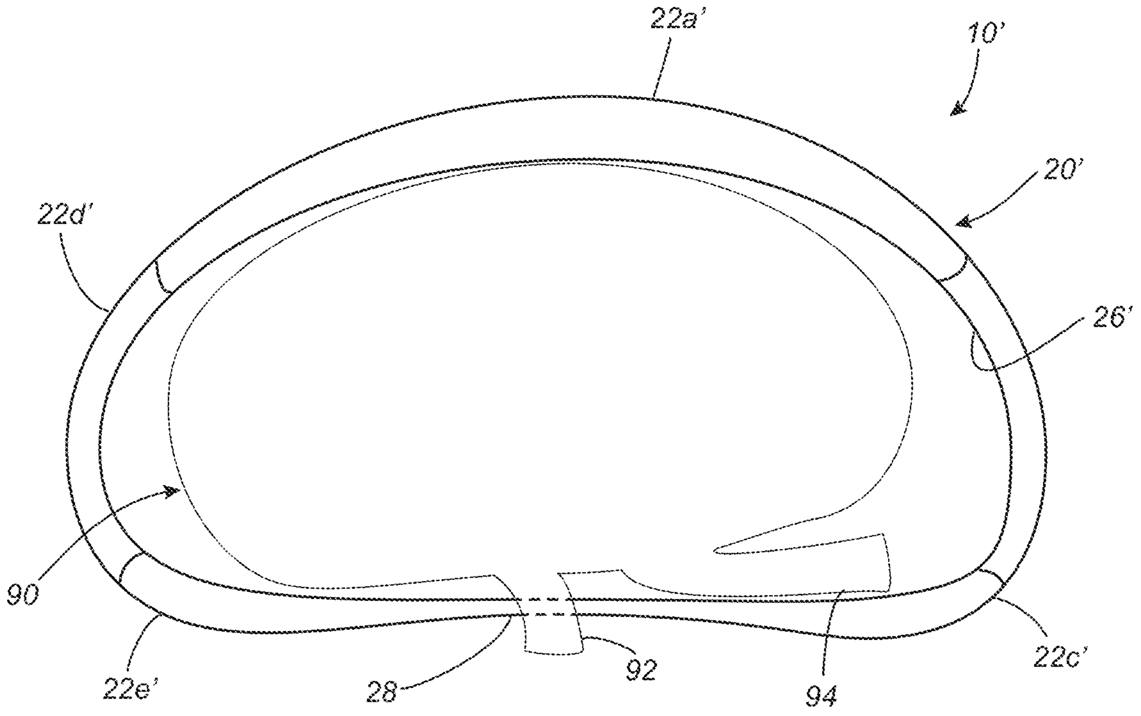
FIG. 5E is a cross-section of the device of FIGS. 5A-5D showing a kidney received in the device.

Alternatively, as shown in FIGS. 5A-5D, a pair of straps 70' may be provided at one end of the lower wall 22*e*', e.g., attached adjacent end wall 22*c*', and may have sufficient length to extend across the opening 28' such that free ends 74' of the straps 70' may be secured to the opposite end of the lower wall 22*e*', e.g., adjacent end wall 22*d*'. The housing 20' and ends 74' of the straps 70' may include cooperating connectors (not shown) that may be used to releasably secure the straps 70', e.g., to secure the organ 90 within the housing 20', e.g., as shown in FIG. 5E. As shown in FIG. 5A, the straps 70' may be spaced apart such that the arterial and venous vessels 92 of the organ may extend from the cavity 26' between the straps 70', which may facilitate completing an anastomosis, as described elsewhere herein. In the example of the organ being a kidney, the ureter 94 may be located within the cavity 26', e.g., to keep the ureter out of the surgical field during the anastomosis, as also described further elsewhere herein.

Optionally, the device 10 of FIG. 3 (or any of the other devices herein) may include one or more additional closure features, e.g., to at least partially close the opening 28. For example, one or more drawstrings may be provided at least partially around the perimeter of the opening 28 (not shown), which may be pulled or otherwise manipulated to at least partially constrict the opening 28, e.g., before or after securing the straps 70. The drawstrings may then be tied or otherwise secured to maintain the constricted opening 28. When it is desired to remove the organ, the drawstrings may be untied, severed, unlooped, and/or otherwise released to allow the opening 28 to be expanded. In addition or alternatively, such drawstrings or other constrainment features (not shown) may be provided at other locations within the walls of the housing, if desired, to allow the housing to be compressed after receiving an organ.

In addition or alternatively, the device 10 may include one or more straps, pockets, or other features (not shown) to facilitate storage and/or control exposure of one or more structures extending from the organ 90 received in the cavity 26. For example, in the case of a kidney, it may be desirable to expose the renal vessels 92, e.g., to facilitate anastomosis to the recipient's iliac vessels, while holding the kidney's hilar fat and/or ureter out of the way, e.g., by securing the ureter adjacent or within the opening 28.

Figure 6A:
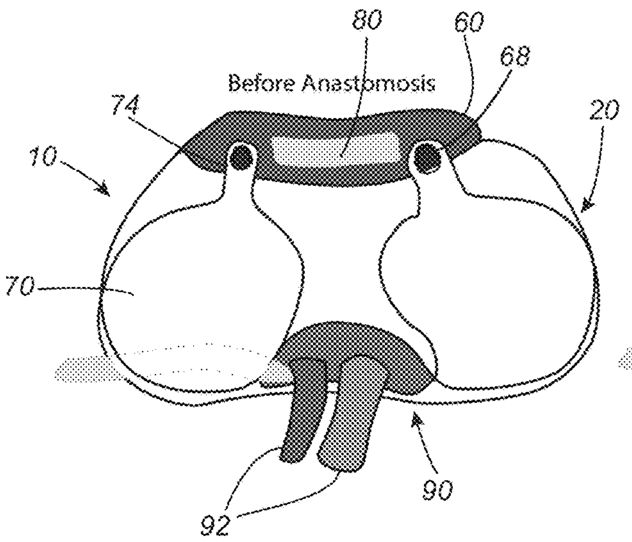
FIGS. 6A-6D show an exemplary method for using a hypothermic device, such as the device of FIG. 3, during a transplantation procedure.
Figure 6B:
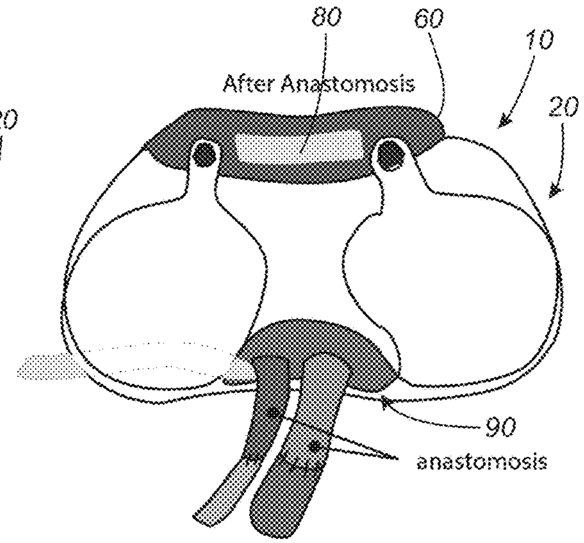

Optionally, the device 10 of FIG. 3 (or any of the other devices herein) may include one or more electrical components. For example, one or more temperature sensors (not shown) may be provided on or otherwise adjacent the inner surface 32 of the housing 20 for measuring the temperature of the organ 90 received in the cavity 26. The sensor(s) may be coupled to a processor and/or output device carried on the housing 20, e.g., to provide an output of the measured temperature to a surgeon and/or other users of the device 10. For example, as shown in FIGS. 6A and 6B, a display 80 may be mounted on handle 60 that may be coupled to the sensor(s) to display a numerical value of the measured temperature such that the user may confirm that the organ 90 is being maintained at a desired temperature. In addition or alternatively, other output devices may be provided, e.g., one or more lights or color changing material that may emit colors corresponding to the status of the organ 90, e.g., including a green light to indicate the organ 90 is being maintained within a desired temperature range and/or a yellow or red light to indicate when the organ 90 is outside the desired range. Alternatively, such a display and/or indicator 80' may be provided at other locations, e.g., on an upper wall 22*a*' of the housing 20', e.g., as shown in FIG. 5A.

Optionally, the device 10 of FIG. 3 (or any of the other devices herein) may include a wireless transmitter, e.g., coupled to sensor(s) and/or display or processor, e.g., to transmit temperature data to a remote electronic device, such as a cellphone, tablet, computer, and the like (not shown) to allow a user to monitor temperature. In addition or alternatively, the device 10 may include one or more additional sensors, e.g., an ultrasound and/or doppler sensor that may be coupled to a processor (and/or communicate to a remote device) to one or more characteristics of the organ 90 received in the cavity 26, e.g., to assess vascular flow metrics (including resistive indices), kidney appearance, and/or may acquire sub-capsular images. In addition or alternatively, the device 10 may include a GPS tracking device (not shown), which may be coupled to the processor and/or wireless transmitter to allow the location of the device 10 to be monitored, e.g., during transport.

Optionally, the device 10 of FIG. 3 (or any of the other devices herein) may also include one or more light sources, e.g., one or more LEDs (not shown) mounted to the housing 20, e.g., around or otherwise adjacent the opening 28, which may be activated to illuminate the area adjacent the opening 28, e.g., to illuminate the surgical field during anastomosis. In addition or alternatively, the device 10 may include a timer (not shown), e.g., mounted on the handle 60 and/or included on the display 80, that may be used to monitor elapsed time.

Turning to FIGS. 6A-6D, an exemplary method is shown for using a device 10, such as the device shown in FIG. 3 (although the methods are applicable to all of the devices described herein. At the beginning of Stage 3, e.g., as shown in FIGS. 1A and 1B, the kidney or other transplant organ 90 may be removed from the transport medium used to cool the organ 90 during Stage 2, e.g., a perfusion machine or cold storage within a cooler (not shown). The organ 90 may then undergo back-table preparation for transplantation in the standard manner and, upon completion, the organ 90 may be kept within a slush (Wisconsin) solution surrounded by ice to maintain its temperature at 4±3° C.

Optionally, the device 10 may be used during the organ procurement and/or transportation periods, e.g. to maintain the organ 90 within a specific temperature range and/or to provide information on temperature variance during transportation. In addition or alternatively, the device 10 may be used during the back-table preparation of the organ 90 prior to implantation into the recipient.

Before use, the device 10 may be stored in a freezer, refrigerator, and/or under other conditions, e.g., to prevent the phase-change material or other coolant from warming. When the device 10 is to be used, e.g., immediately before or during any stage of the transplantation procedure, the device 10 may be removed from storage and allowed to adopt an appropriate temperature for receiving the organ 90.

For example, during exposure of the iliac vessels in the recipient, the device 10 may be removed from the freezer and placed on ice or within a slush machine for a defined time period. Immediately prior to anastomosis, the organ 90 may be removed from the slush solution, placed within the cavity 26 of the device 10, and the securing straps 70 may be applied to hold the organ 90 inside the device 10, e.g., as shown in FIG. 6A. Optionally, the device 10, and organ 90 therein, may then be connected to one or more structures adjacent the recipient, e.g., one or more retractors (not shown) to stabilize the device 10 relative to the surgical field. For example, the handle 60 may be secured to retractors or other structures, which may facilitate stabilizing the device 10, e.g., during an open procedure, a minimally invasive procedure, or during a robotic procedure.

Optionally, a timer on the device 10 may be activated to initiate tracking of the anastomosis time and/or organ surface temperature measurements. With respect to kidney transplants, the device 10 may hold the kidney 90 such that the renal vein and renal artery 92 are exposed, and the device 10 may be positioned adjacent the recipient's body such that the renal vein and renal artery 92 of the kidney 90 are easily accessible for sew-in while the kidney 90 remains inside the device 10 and cool, e.g., as shown in FIG. 6B. The vein and artery 92 are then sewn to their respective iliac vessels within the recipient. Optionally, the device 10 may include one or more straps, pockets, or other features (not shown) to facilitate storage and/or control exposure of one or more structures extending from the organ 90 received in the cavity 26. For example, in the case of a kidney, it may be desirable to expose the iliac vessels 92, e.g., to facilitate anastomosis to the recipient's vessels, while holding the kidney's ureter out of the way, e.g., by securing the ureter adjacent or within the opening 28.

Figure 6C:
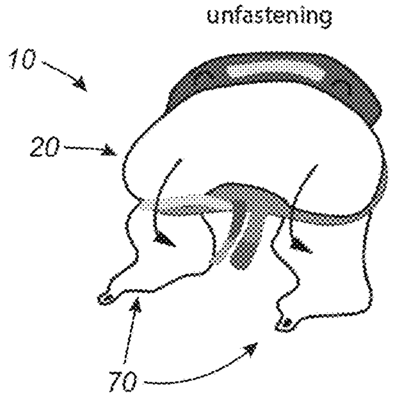
Figure 6D:
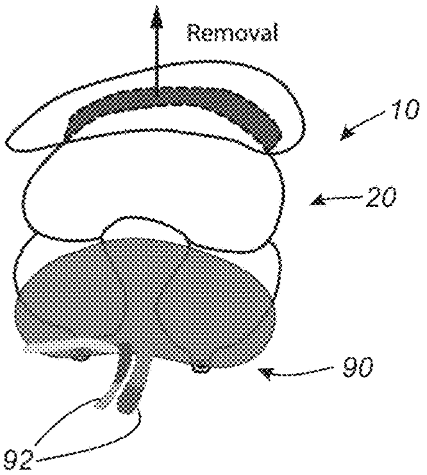

Following completion of the anastomosis and unclamping of the recipient's iliac artery and vein, the timer on the device 10 (if included) may be pressed again to signal the end of anastomosis, and the total anastomosis time may then be recorded. As shown in FIGS. 6C and 6D, the straps 70 may be released from the housing 20, and the device 10 may be removed from around the organ 90 and removed from the surgical field. Thus, it will be appreciated that the device 10 may facilitate cooling of the organ 90, while allowing ready access to the vessels 92 of the organ 90, which may facilitate workflow during the implantation procedure, e.g., facilitating anastomosis.

Ureter anastomosis to the bladder and/or other remaining procedures may then proceed per SOC. Optionally, the organ 90 may remain within the device 20 after completing the anastomosis procedure, e.g., while perfusing the organ 90 and/or to regulate rewarming of the organ post-procedure.

Figures 7A, 7B, 7C:
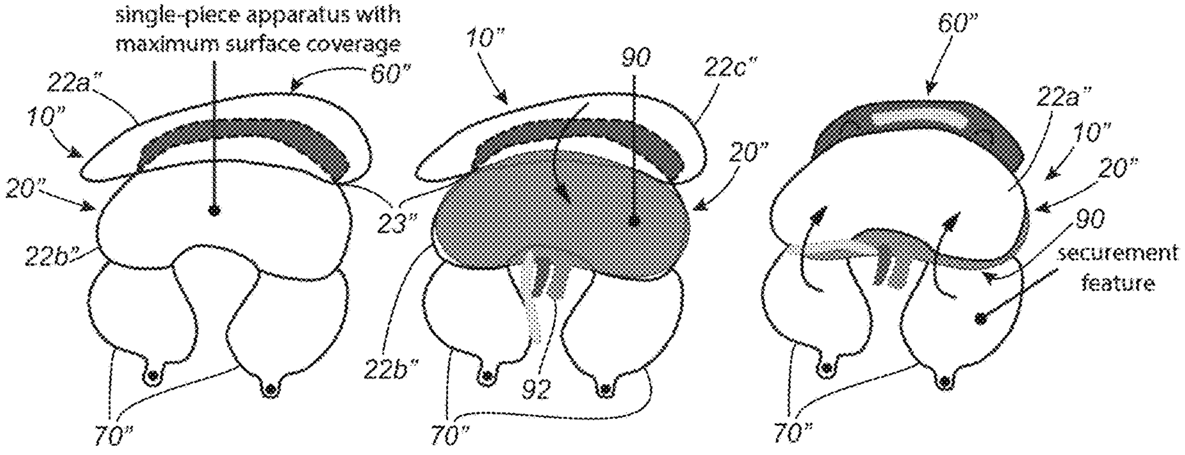
FIGS. 7A-7C show an alternative example of a hypothermic device that includes a flexible housing that may be wrapped around an organ.

Turning to FIGS. 7A-7C, an alternative example of a hypothermic device 10' is shown, which may be generally constructed and include any of the features described above with respect to device 10. In this alternative, the housing 20' includes an upper wall 22*a*' and a lower wall 22*b*' that are attached along common edge 23'. The walls 22*a*', 22*b*' may be integrally formed together or separately and then attached along the edge 23', e.g., using similar materials and methods as described elsewhere herein. One or both walls 22*a*', 22*b*' may include a cooling layer, e.g., including one or more regions of phase-change material (not shown), similar to device 10. For example, the walls 22*a*', 22*b*' may be movable relative to one another, e.g., such that the housing 20' may be opened, e.g., lain flat, to accommodate placing an organ 90 within the housing 20.' For example, as shown in FIG. 7B, with the housing 20' open, the organ 90 may be placed on the lower wall 22*b*' and then the upper wall 22*a*' may be folded or otherwise positioned over the organ 90, as shown in FIG. 7C, whereupon the straps 70' may be secured, similar to the device 10.

With this housing 20', the side edges of the walls 22*a*', 22*b*' extending from the common end 23' may remain separate, e.g., simply placed adjacent one another and/or partially overlapped. Alternatively, one or more drawstrings, clasps, and/or other connectors (not shown) may be provided along the side edges that may be connected to close and/or further secure the side edges together. Once the organ 90 is secured within the housing 20,' the device 10' may be used similar to other devices herein.

Figure 8:
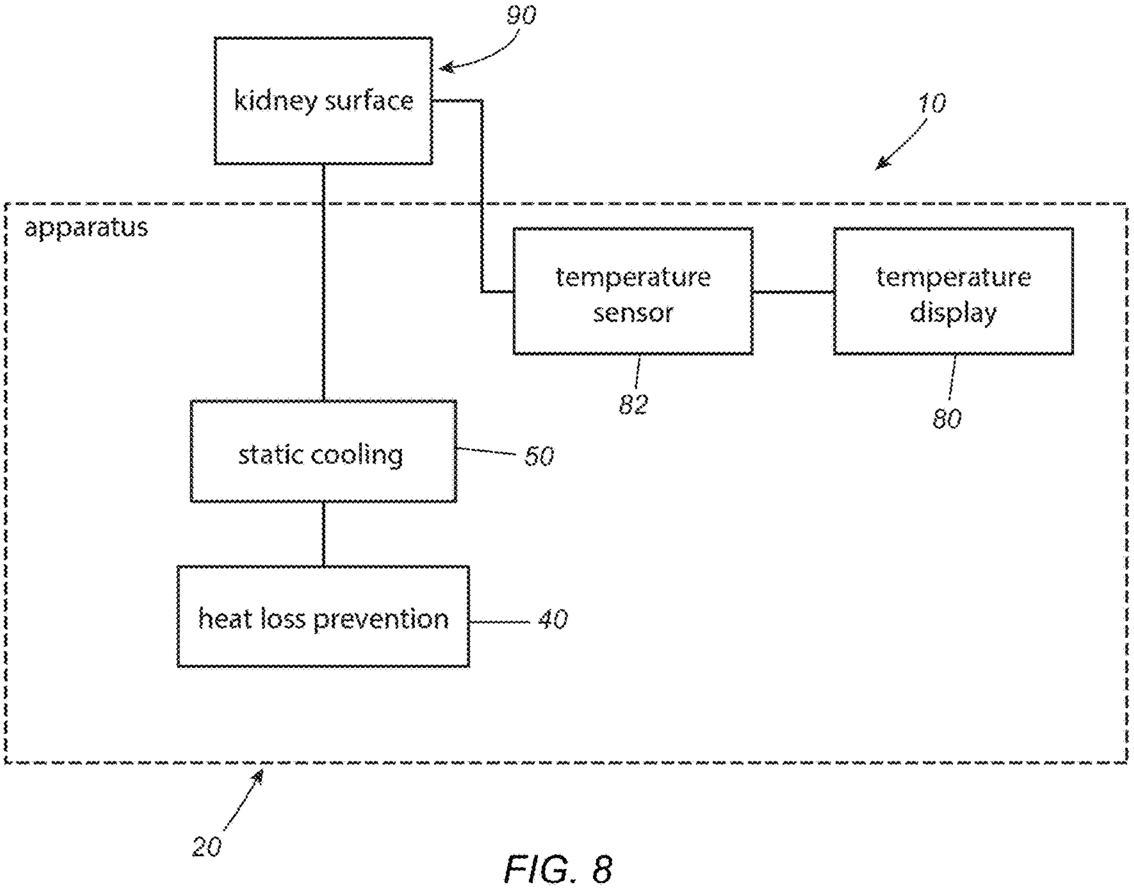
FIG. 8 is a schematic of an example of a device for regulating temperature of an organ including internal static cooling.

Turning to FIG. 8, a schematic of a hypothermic device is shown, which may include any of the components described above with respect to the device 10. As shown, the housing 20 may include a static cooling component 50, e.g., a cooling layer containing phase-change material encapsulated or otherwise secured within one or more walls of the housing 20 (not shown). For example, similar to the device 10, the housing 20 may include an outer layer 40 overlying the cooling component, e.g., including thermally insulative materials to minimize heat loss through the outer surface of the device 10. It will be appreciated that other static cooling materials and/or systems may be provided within the housing 20 to regulate the temperature of an organ 90 received within the housing 20. As shown, the device 10 also includes a temperature sensor 82, e.g., on or adjacent an inner surface of the housing 20, coupled to a display 80, which may provide a readout of the temperature of the organ 90, e.g., as described elsewhere herein.

Figure 9:
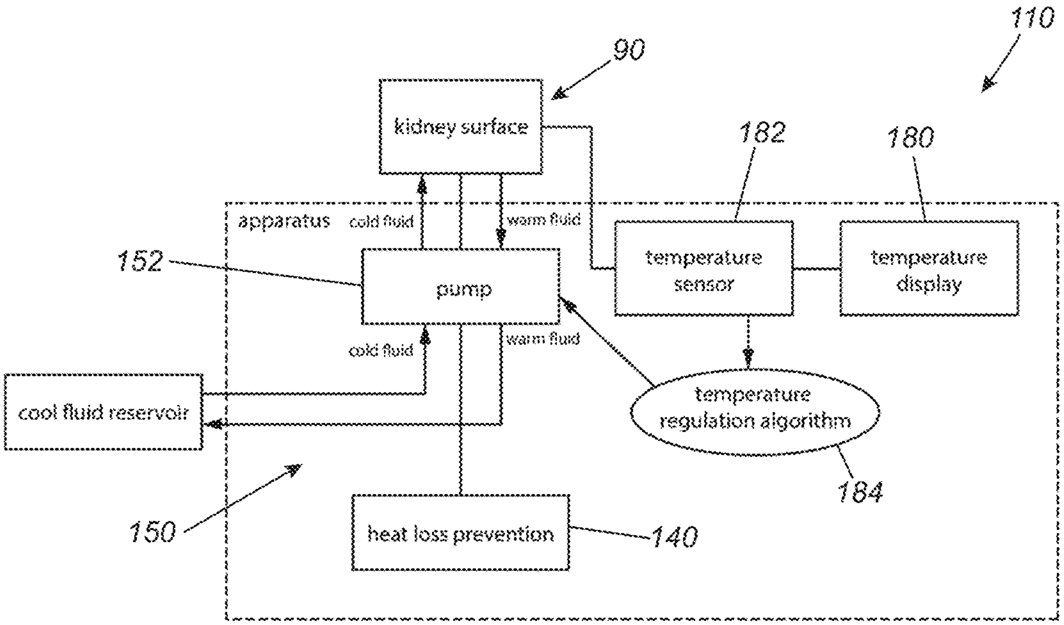
FIG. 9 is a schematic of another example of a device for regulating temperature of an organ where the cooling layer includes a plurality of fluid channels and a pump for circulating coolant through the fluid channels from an external reservoir.

Turning to FIG. 9, a schematic of another example of a hypothermic device 110 is shown that includes a housing 120 containing a cooling component 150, e.g., within one or more walls of the housing 120, and may include an outer layer or other heat loss prevention component 140, similar to the other devices herein. As shown, the device 110 includes a temperature sensor 182 coupled to a display 180 and, optionally, may include any other features or components described with respect to the other devices herein.

Figure 10:
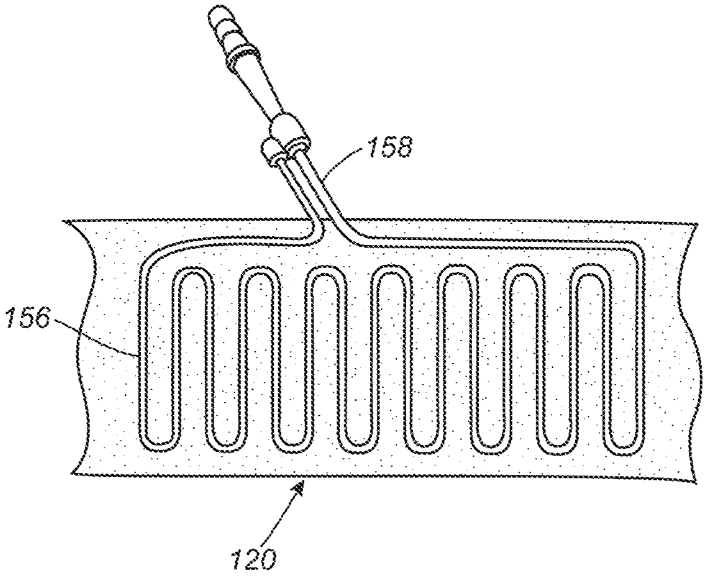
FIG. 10 shows an example of a device for regulating temperature of an organ where the cooling layer includes a plurality of fluid channels for receiving coolant from an external source, which may be included in the device of FIG. 9.

Unlike the previous devices, the cooling component 150 includes an active cooling system including a pump 152, which may be used to circulate coolant within one or more walls of the housing 120, e.g., in an open-loop configuration. For example, the pump 152 may communicate with an external reservoir or other source of coolant 154 and a plurality of fluid channels 154 within one or more walls of the housing 120 (or otherwise provided adjacent the inner surface), e.g., as shown in FIG. 10. As shown in FIG. 10, external tubing 158 may connect the reservoir 154 with the housing 120 to deliver and remove coolant circulated by the pump 152. The reservoir 154 contains a flowable coolant, e.g., in liquid, gas, or mixed phase, that may be cooled and circulated through the channels to transfer thermal energy from an organ 90 received within the housing 120. For example, the coolant may include one or more of a flowable gel, such as silica gel, microsphere gels, alcohol, chilled water (e.g., at between about two and four degrees Celsius (2-4° C.) or other desired temperatures), a set of flowable chemicals that produce an endothermic reaction when mixed, and the like.

Optionally, the pump 152 or reservoir 154 may include a refrigeration or other treatment system, e.g., a heat exchanger (not shown), for removing thermal energy from the coolant, e.g., after being circulated through the channels 156, to maintain the organ 90 at a desired temperature. Alternatively, the reservoir 154 may include a source container of coolant and a water receptacle (not shown) such that coolant from the initial source may be circulated through the channels 156 and then removed and stored without being treated and returned back into the channels 156.

For example, a processor 184 coupled to the pump 152 may include a temperature regulation algorithm that may control operation of the pump 152 and/or reservoir 154 based on signals from the temperature sensor 182 to maintain the target temperature. This may include modifying a flow rate of the coolant through the channels 156 and/or adjusting the temperature of the coolant delivered by the pump 152.

Figure 11:
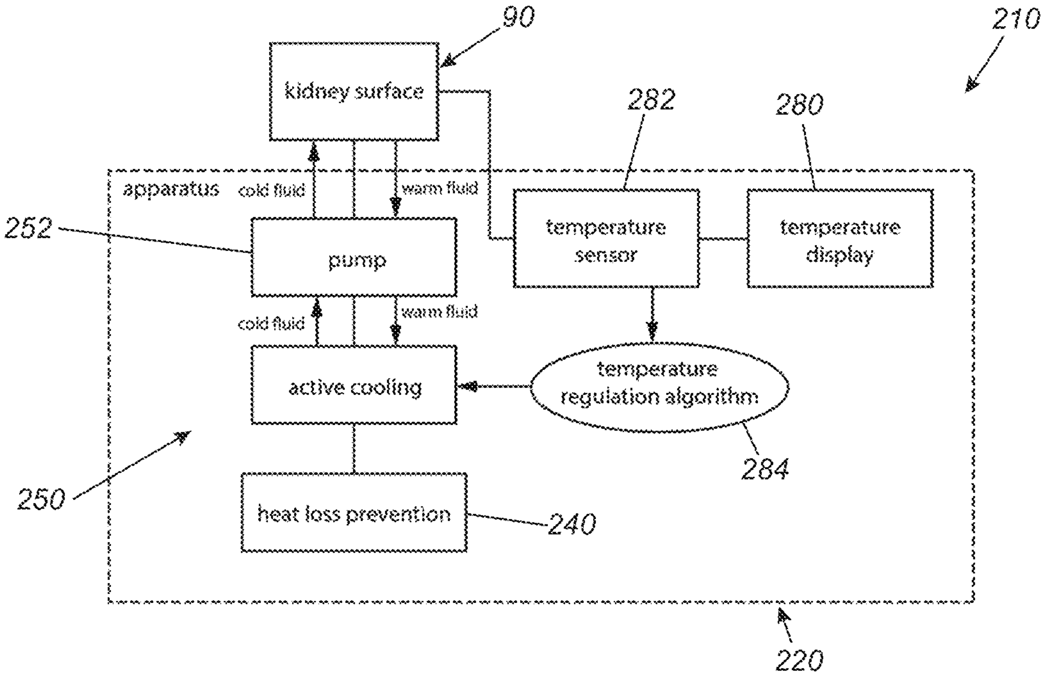
FIG. 11 is a schematic of another example of a device for regulating temperature of an organ where the cooling layer includes a plurality of fluid channels and a pump for circulating coolant internally through the fluid channels.

Alternatively, a device may be provided that eliminates any external reservoirs and/or tubing. For example, as shown in FIG. 11, a device 210 including a closed-loop configuration of active cooling 250 may be provided. For example, a pump 252 may communicate with an internal reservoir (not shown) within the housing 220 and a plurality of fluid channels (also not shown) to circulate coolant through one or more walls of the housing 220. The pump 252 may be embedded or otherwise mounted to the housing 220 or, alternatively, may be external to the housing 220 and may communicate with the fluid channels via one or more sections of tubing (not shown). The device 210 may include a temperature regulation algorithm, e.g., a processor 284 coupled to the temperature sensor 282 and pump 252 to control one or more parameters of the cooling system to maintain the organ 90 at a desired temperature.

Figure 13:
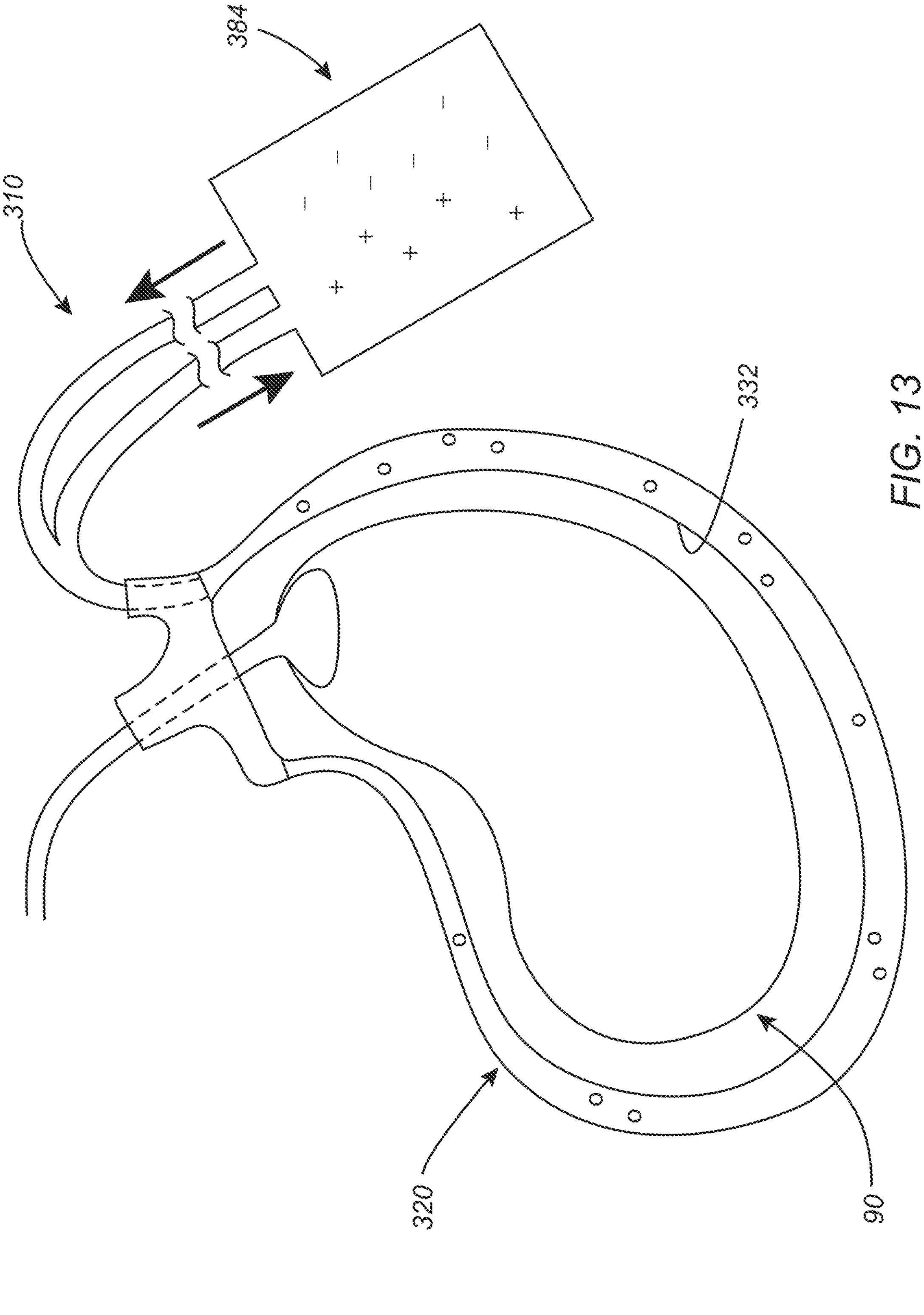
FIG. 13 shows an example of a device for regulating temperature of an organ where the cooling layer includes a plurality of thermoelectric elements controlled by an external heat exchanger.

Turning to FIG. 13, in a further alternative, a hypothermic device 310 is shown that includes a multiple layer housing 320 including a thermoelectric cooling system. For example, one or more walls of the housing 320 may include piezoelectric elements (not shown), e.g. adjacent the inner surface 332, that may be coupled to a heat exchanger, processor and/or power source 384 to control activation and/or operation of the elements. For example, the elements may include layers of dissimilar semiconductors that may use the Peltier effect to absorb thermal energy from the organ 90 received within the housing 320, e.g., to maintain the organ 90 within a desired temperature range.

Figures 12A, 12B, 12C, 12D:
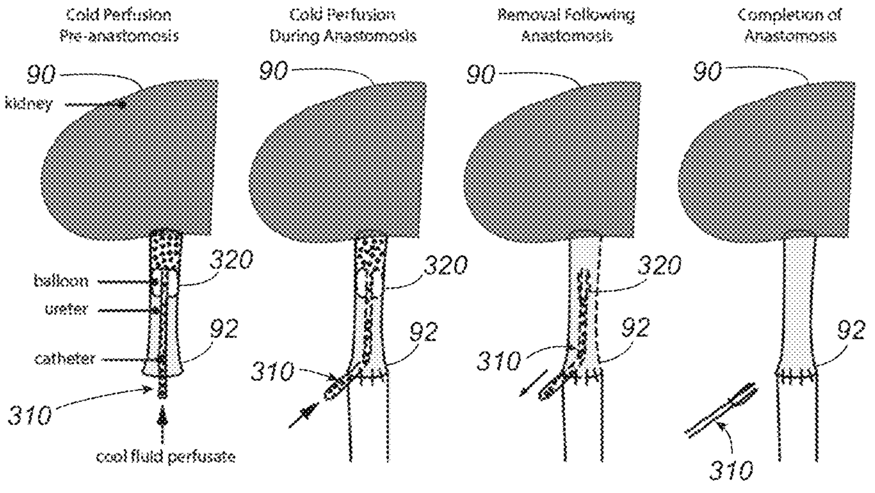
FIGS. 12A-12D show an exemplary method for delivering cold perfusion to an organ for transplantation.

Turning to FIGS. 12A-12D, an exemplary system and method for providing open-loop cooling of an organ, e.g., kidney 90, is shown. For example, as shown in FIG. 12A, a catheter 310 with a balloon tip 320 may be inserted into the ureter 92 and inflated. As shown in FIG. 12B, a cooling fluid or gel, such as chilled 2-4° C. Wisconsin solution, or similar preservation solutions may be instilled into the kidney 90 via an infusion lumen of the catheter 310 and removed via a removal lumen (not shown) of the catheter 310 to maintain a cooled kidney. In another example, the cooled fluid is instilled and removed cyclically via a single lumen catheter. As shown in FIGS. 12C and 12D after completing the anastomosis procedure, the balloon 320 may be deflated and the catheter 310 removed.

In describing representative examples, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for regulating temperature of an organ being transplanted from a donor to a recipient, comprising:

a housing comprising one or more walls surrounding an interior cavity sized to receive an organ and an opening for accessing the cavity;

a temperature sensor adjacent the inner surface for measuring temperature of the organ received in the cavity; and an output device to provide an output of the measured temperature;

wherein one or more of the walls comprises:

an inner layer defining an inner surface for contacting the organ placed in the cavity;

an outer layer defining an outer surface of the housing; and a cooling layer between the inner and outer layers configured to absorb thermal energy from the organ within the cavity through the inner layer; and wherein the output device comprises a light or color changing material configured to emit one or more colors corresponding to a status of the organ.

2. The device of claim 1, wherein the cooling layer comprises a phase-change material.

3. The device of claim 2, wherein the phase-change material is composed to maintain a temperature within the cavity between about one and seven degrees Celsius (1-7° C.).

4. The device of claim 2, wherein the phase-change material is encapsulated between the inner and outer layers.

5. The device of claim 2, wherein the phase-change material comprises n-tetradecane (n-TD).

6. The device of claim 2, wherein the phase-change gel is contained within compartments or cells between the inner and outer layers, with the compartments being at least partially isolated from one another.

7. The device of 2, wherein the phase-change material comprises 1-Decanol (Decyl alcohol).

8. The device of claim 1, wherein the outer layer comprises material having a low thermal conductivity to minimize exposure of the cooling layer to exterior temperatures.

9. The device of claim 1, wherein the housing comprises a flexible jacket sized to receive the organ within the cavity such that the organ contacts the inner surface.

10. The device of claim 1, further comprising one or more fasteners for at least partially closing the opening to secure the organ received within the cavity.

11. The device of claim 1, further comprising a handle extending from the housing to facilitate manipulation of the housing.

12. The device of claim 1, further comprising an indicator on the housing configured to provide a visual indication of an anatomical orientation of the organ received within the cavity.

13. The device of claim 1, further comprising:

a temperature sensor adjacent the inner surface for measuring temperature of the organ received in the cavity; and an output device to provide an output of the measured temperature.

14. The device of claim 1, wherein the one or more colors comprise a first color that indicates the organ is being maintained within a desired temperature range and second color that indicates when the organ is outside the desired temperature range.

15. The device of claim 1, further comprising a timer configured to be activated during a surgical procedure to provide an indication of elapsed time during the procedure.

16. The device of claim 1, further comprising a GPS tracking device mounted on the housing to allow the location of the device to be monitored.

17. The device of claim 1, further comprising one or more lights adjacent the opening to illuminate a surgical field adjacent the opening.

18. The device of claim 1, wherein the one or more colors comprise a first color that indicates the organ is being maintained within a desired temperature range and a second color that indicates when the organ is outside the desired temperature range.

19. The device of claim 1, wherein the color changing material comprises an indicator on an upper wall of the housing.

20. A device for regulating temperature of an organ being transplanted from a donor to a recipient, comprising:
- a housing comprising one or more walls surrounding an interior cavity sized to receive an organ and an opening for accessing the cavity;
- one or more straps extending from the housing adjacent the opening, a free end of each strap and the housing comprise cooperating connectors for securing the strap to the housing across the opening;
- a temperature sensor adjacent the inner surface for measuring temperature of the organ received in the cavity; and
- an output device to provide an output of the measured temperature;
- wherein one or more of the walls comprises:
  - an inner thermally conductive layer defining an inner surface for contacting the organ placed in the cavity;
  - an outer thermally insulative layer defining an outer surface of the housing; and
  - a cooling layer between the inner and outer layers comprising a phase-change material configured to absorb thermal energy from the organ within the cavity through the inner layer; and
- wherein the output device comprises a light or color changing material configured to emit one or more colors corresponding to a status of the organ.

21. The device of claim 20, wherein the one or more straps comprise a pair of straps extending from one edge of the opening adjacent one another, and wherein free ends of the straps and the housing comprise cooperating connectors for securing the straps to the housing across the opening such that a portion of the opening remains open to allow vessels from the organ received within the cavity to extend from the housing.

22. The device of 20, further comprising a handle extending from the housing to facilitate manipulation of the housing.

23. The device of claim 20, further comprising an indicator on the housing configured to provide a visual indication of an anatomical orientation of the organ received within the cavity.

24. The device of claim 20, wherein the one or more colors comprise a first color that indicates the organ is being maintained within a desired temperature range and a second color that indicates when the organ is outside the desired temperature range.

25. The device of claim 20, wherein the color changing material comprises an indicator on an upper wall of the housing.

26. A device for regulating temperature of an organ being transplanted from a donor to a recipient, comprising:
- a housing comprising one or more walls surrounding an interior cavity sized to receive an organ and an opening for accessing the cavity;
- wherein one or more of the walls comprises:
  - an inner layer defining an inner surface for contacting the organ placed in the cavity;
  - an outer layer defining an outer surface of the housing; and
  - a cooling layer between the inner and outer layers configured to absorb thermal energy from the organ within the cavity through the inner layer;
- wherein the outer layer comprises material having a low thermal conductivity to minimize exposure of the cooling layer to exterior temperatures, and
- wherein the outer wall comprises one or more air pockets or foam fillers to reduce the thermal conductivity of the outer layer.

* * * * *